(12) United States Patent
Raquel et al.

(10) Patent No.: US 10,429,320 B2
(45) Date of Patent: Oct. 1, 2019

(54) METHOD FOR AUTO-LEARNING TOOL MATCHING

(71) Applicant: KLA-Tencor Corporation, Milpitas, CA (US)

(72) Inventors: Francis Raquel, Danville, CA (US); Matthew Manzer, Campbell, CA (US); Christopher Lee, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1035 days.

(21) Appl. No.: 14/270,148

(22) Filed: May 5, 2014

(65) Prior Publication Data

US 2014/0358480 A1 Dec. 4, 2014

Related U.S. Application Data

(60) Provisional application No. 61/831,046, filed on Jun. 4, 2013.

(51) Int. Cl.
*G01N 21/95* (2006.01)
*G01M 99/00* (2011.01)

(52) U.S. Cl.
CPC ...... *G01N 21/9501* (2013.01); *G01M 99/008* (2013.01); *G01N 2201/126* (2013.01)

(58) Field of Classification Search
CPC ............ G01M 99/008; G01N 21/9501; G01N 2201/126
See application file for complete search history.

(56) References Cited

U.S. PATENT DOCUMENTS

| | | | |
|---|---|---|---|
| 5,607,800 A | 3/1997 | Ziger | |
| 5,655,110 A * | 8/1997 | Krivokapic | ......... G03F 7/70625 700/95 |
| 5,739,909 A | 4/1998 | Blayo et al. | |
| 5,867,276 A | 2/1999 | McNeil et al. | |
| 5,889,593 A | 3/1999 | Bareket | |
| 5,963,329 A | 10/1999 | Conrad et al. | |
| 6,429,943 B1 | 8/2002 | Opsal et al. | |
| 6,625,512 B1 | 9/2003 | Goodwin | |

(Continued)

FOREIGN PATENT DOCUMENTS

KR 10-2009-0132537 A 12/2009

*Primary Examiner* — Andrew Schechter
*Assistant Examiner* — Lina M Cordero
(74) *Attorney, Agent, or Firm* — Suiter Swantz pc llo

(57) ABSTRACT

The present disclosure is directed to a method of tool matching that employs an auto-learning feedback loop to update a library of key parameters. According to the method, measurements are performed on a control wafer to collect a set of parameters associated with the process/analysis tool that is being matched. When deviated parameters correlate to a correctable tool condition (i.e. a tool matching event), the parameters are added to the library of key parameters. These key or critical parameters may be monitored on a more frequent basis to identify deviations that have a strong likelihood of matching with a correctable tool condition. The tool matching methodology advantageously allows for monitoring of an automatically updated list of key parameters instead of needing to look at the full set of parameters collected from a control wafer each time. As such, tool matching can be performed on a more frequent basis.

17 Claims, 4 Drawing Sheets

(56) References Cited

U.S. PATENT DOCUMENTS

| | | | | |
|---|---|---|---|---|
| 6,639,663 B1* | 10/2003 | Markle | | G01N 21/47 250/559.09 |
| 6,813,034 B2 | 11/2004 | Rosencwaig et al. | | |
| 6,819,426 B2 | 11/2004 | Sezginer et al. | | |
| 7,765,515 B2* | 7/2010 | Ying | | G03F 1/36 716/52 |
| 8,543,557 B2* | 9/2013 | Aikens | | G01N 21/47 707/700 |
| 2002/0051567 A1* | 5/2002 | Ganz | | G03F 7/70483 382/152 |
| 2003/0028358 A1* | 2/2003 | Niu | | G01B 11/24 703/2 |
| 2003/0076511 A1* | 4/2003 | Aikens | | G01N 21/47 356/636 |
| 2006/0114437 A1 | 6/2006 | Akhssay et al. | | |
| 2007/0233404 A1* | 10/2007 | Lally | | G01N 21/95607 702/35 |
| 2008/0052021 A1* | 2/2008 | Morinaga | | G01N 21/8851 702/81 |
| 2008/0286885 A1* | 11/2008 | Izikson | | G05B 21/02 438/7 |
| 2009/0080759 A1 | 3/2009 | Bhaskar et al. | | |
| 2009/0187383 A1* | 7/2009 | Li | | G01B 11/06 702/191 |
| 2009/0319075 A1* | 12/2009 | Tian | | G01N 21/9501 700/121 |
| 2011/0301847 A1* | 12/2011 | David | | B24B 37/013 702/1 |
| 2012/0226644 A1* | 9/2012 | Jin | | G06N 3/08 706/19 |
| 2013/0148130 A1* | 6/2013 | Li | | G01B 11/24 356/601 |
| 2013/0304408 A1* | 11/2013 | Pandev | | H01L 22/20 702/83 |
| 2014/0201693 A1* | 7/2014 | Saleh | | H01L 22/12 716/102 |

\* cited by examiner

METHOD FOR AUTO-LEARNING TOOL MATCHING

PRIORITY

The present application claims priority under 35 U.S.C. § 119(e) to U.S. Provisional Patent Application Ser. No. 61/831,046, titled METHOD FOR AUTO-LEARNING WAFERLESS TOOL MATCHING, By Francis Raquel et al., filed Jun. 4, 2013, which is currently co-pending, or is an application of which currently co-pending application(s) are entitled to the benefit of the filing date. The above-referenced provisional patent application is hereby incorporated by reference in its entirety.

TECHNICAL FIELD

The present disclosure generally relates to the field of tool matching.

BACKGROUND

In modern semiconductor fabrication, there exists a variety of tools for processing (e.g. lithography) and performing analysis (e.g. metrology or inspection) upon a wafers, masks, or other manufactured structures. These tools may experience drifts, debris buildup, or damage over time. As a result, various tool components may need to be adjusted, cleaned, or replaced to maintain process parameters within manufacturing specifications.

Specialized monitor wafers are often used for tool matching. These wafers must be qualified on a healthy tool and shipped out to users. Periodically, the user may run a monitor wafer to determine necessary adjustments or repairs based upon a correlation between deviations in measured parameters of the monitor wafer and one or more correctable tool conditions. Since this process is intrusive to the fabrication process and requires specialized wafers which may need to be replaced from time to time, the current tool matching process is burdensome on users and may not be performed as frequently as needed. To avoid degraded fabrication quality, a less burdensome tool matching process is needed in the art.

SUMMARY

In one aspect, this disclosure is directed to a method of tool matching that employs an auto-learning feedback loop to update a library of key parameters. These key or critical parameters may be monitored on a more frequent basis to identify deviations that have a strong likelihood of matching with a correctable tool condition. The method may include at least the steps of: performing measurements on a control wafer at a first time to determine a first set of parameters associated with tool conditions of a tool for processing, inspecting, or performing metrology upon one or more wafers; comparing the first measured set of parameters against a primary set of parameter thresholds to determine whether or not a parameter of the first measured set of parameters matches a correctable tool condition; determining whether or not the parameter is included in a library of key parameters when the parameter matches a correctable tool condition, the library of key parameters including a secondary set of parameter thresholds that is a subset of the primary set of parameter thresholds; adding the parameter to the library of key parameters when the parameter matches a correctable tool condition and is not represented in the library of key parameters; and reporting whether or not the tool is affected by a correctable tool condition.

In an embodiment, the method may be manifested by tool matching system including a measurement tool with an integrated or communicatively coupled a computing system. The computing system may include at least one processor in communication with a non-transitory signal bearing medium, where the non-transitory signal bearing medium includes stored program instructions for completing one or more steps of the method. For example, the program instructions may include one or more executable instruction sets that cause the processor to: determine, based upon measurements collected from a control wafer at a first time, a first set of parameters associated with tool conditions of a tool for processing, inspecting, or performing metrology upon one or more wafers; compare the first measured set of parameters against a primary set of parameter thresholds to determine whether or not a parameter of the first measured set of parameters matches a correctable tool condition; determine whether or not the parameter is included in a library of key parameters when the parameter matches a correctable tool condition, the library of key parameters including a secondary set of parameter thresholds that is a subset of the primary set of parameter thresholds; add the parameter to the library of key parameters when the parameter matches a correctable tool condition and is not represented in the library of key parameters; and report whether or not the tool is affected by a correctable tool condition. Alerts or reports from the tool matching system may be provided via a user interface and/or sent to a process/analysis tool (i.e. the tool being matched) via a communicative coupling, such as a direct wired/wireless communication link or network.

The measurement tool may include any metrology system known to the art. In some embodiments, for example, the measurement tool may include an optical metrology system with a stage configured to receive a control wafer, at least one illumination source configured to illuminate the control wafer, at least one detector configured to receive illumination reflected, scattered, or radiated from the control wafer, and a computing system in communication with the at least one detector. In the optical metrology-based tool matching system, the computing system may be configured to: determine, based upon illumination detected from the control wafer at a first time, a first set of parameters associated with tool conditions of a tool for processing, inspecting, or performing metrology upon one or more wafers; compare the first measured set of parameters against a primary set of parameter thresholds to determine whether or not a parameter of the first measured set of parameters matches a correctable tool condition; determine whether or not the parameter is included in a library of key parameters when the parameter matches a correctable tool condition, the library of key parameters including a secondary set of parameter thresholds that is a subset of the primary set of parameter thresholds; add the parameter to the library of key parameters when the parameter matches a correctable tool condition and is not represented in the library of key parameters; and report whether or not the tool is affected by a correctable tool condition.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings. In general, FIGS. 1 through 3B illustrate embodiments of a system and method for tool matching that employ an auto-learning feedback loop to update a library of key parameters. As discussed in further detail below, key or critical parameters are identified during full parameter runs on one or more control wafers and are added to the library so that they can be monitored on a more frequent basis to identify deviations that have a strong likelihood of matching with a correctable tool condition. Accordingly, tool match monitoring can occur more frequently (e.g. several times per day) or as a background process with full runs only being performed at relatively infrequent times (e.g. 1 or 2 times per week) or when a key parameter is determined to be out of limit.

Figure 1:
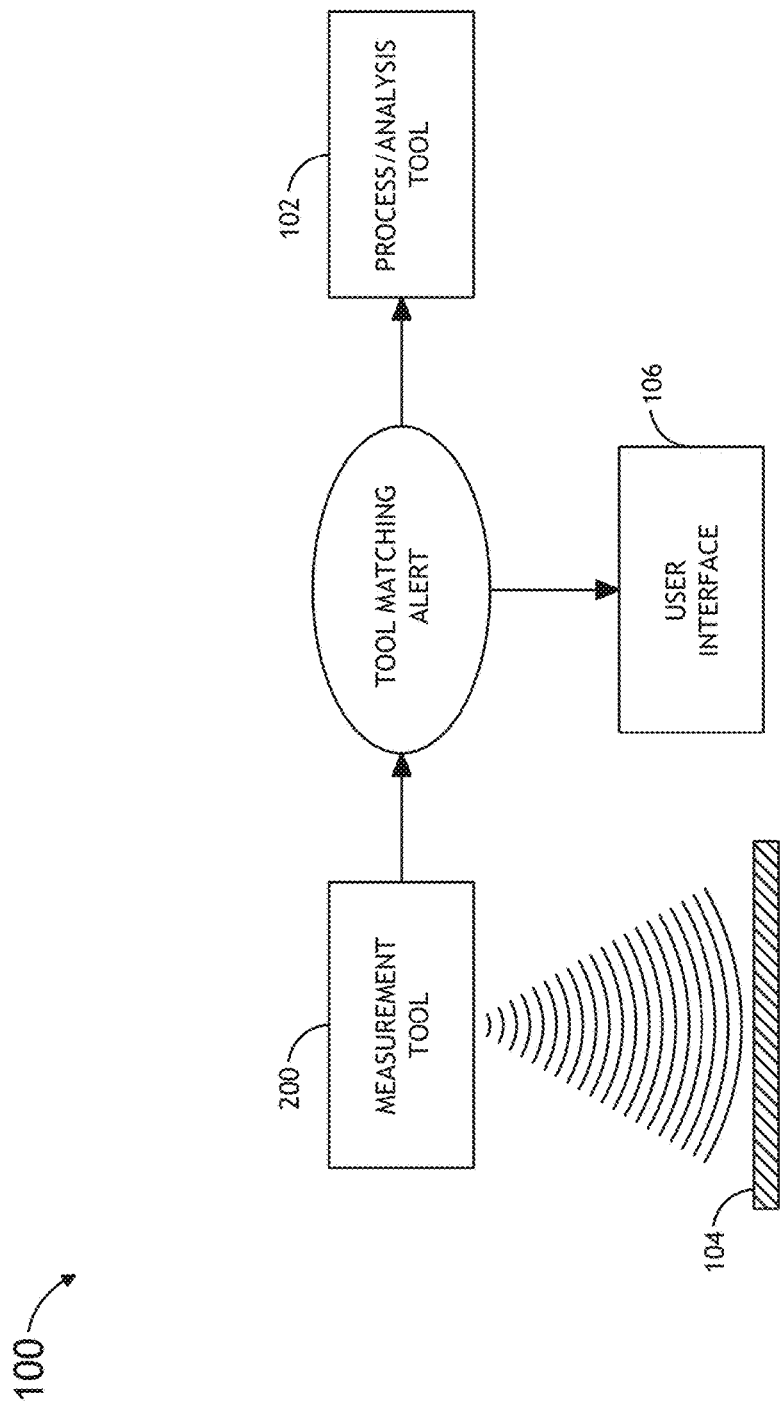
FIG. 1 is a block diagram illustrating tool matching system, in accordance with an embodiment of this disclosure.

FIG. 1 illustrates an exemplary arrangement of a tool matching system 100. In an embodiment, the tool matching system 100 includes a measurement tool 200 that is used to match a process tool 102 (e.g. lithography tool), an analysis tool 102 (e.g. metrology or inspection tool), or the like. In some embodiments, the measurement tool 200 is one and the same as the matched tool 102. For example, a metrology tool 102 may be configured to perform tool matching steps (to match itself) at pre-scheduled and/or user-selected times or upon the occurrence of one or more specified events (e.g. at startup, after a number of runs). Alternatively, the measurement tool 200 may be included in or communicatively coupled with the matched tool 102. In other embodiments, the measurement tool 200 may be completely separate from the matched tool 102. Further, it is contemplated that one measurement tool 200 may be enabled to match a plurality of process/analysis tools 102 and the like.

The measurement tool 200 may include (see, e.g., FIG. 2) or may be communicatively coupled with a computing system 212. The computing system 212 may include at least one processor in communication with a non-transitory signal bearing carrier medium 214, such as a hard-disk drive (HDD), solid-state disk (SSD), flash drive, optical drive, or any other storage device; where the carrier medium 214 includes stored program instructions 216 executable by the processor to carrier out the steps of the tool matching methodology that is described herein. For example, the computing system 212 may be configured to perform steps of the tool matching methodology to determine a tool matching status and may be further configured to generate alerts, reports, or control data, which may be communicated to a user via a communicatively coupled user interface 106 (e.g. a display or audio source), transmitted over a communication link or network to the matched tool 102, or fed back into the measurement tool 200. When parameters measured from control wafer 104 match a correctable tool condition, the matched tool 102 and/or the measurement tool 200 may be configured to adjust various tool settings or parameters according to an alert, report, or control signal associated with the correctable tool condition, or the user may perform any steps needed to remove the correctable tool condition based upon an alert or report received via the user interface 106. Both tools 102 and 200 may use the same wafer data information to self-adjust or add key parameters to the library based on matching state and previous conditions.

Figure 2:
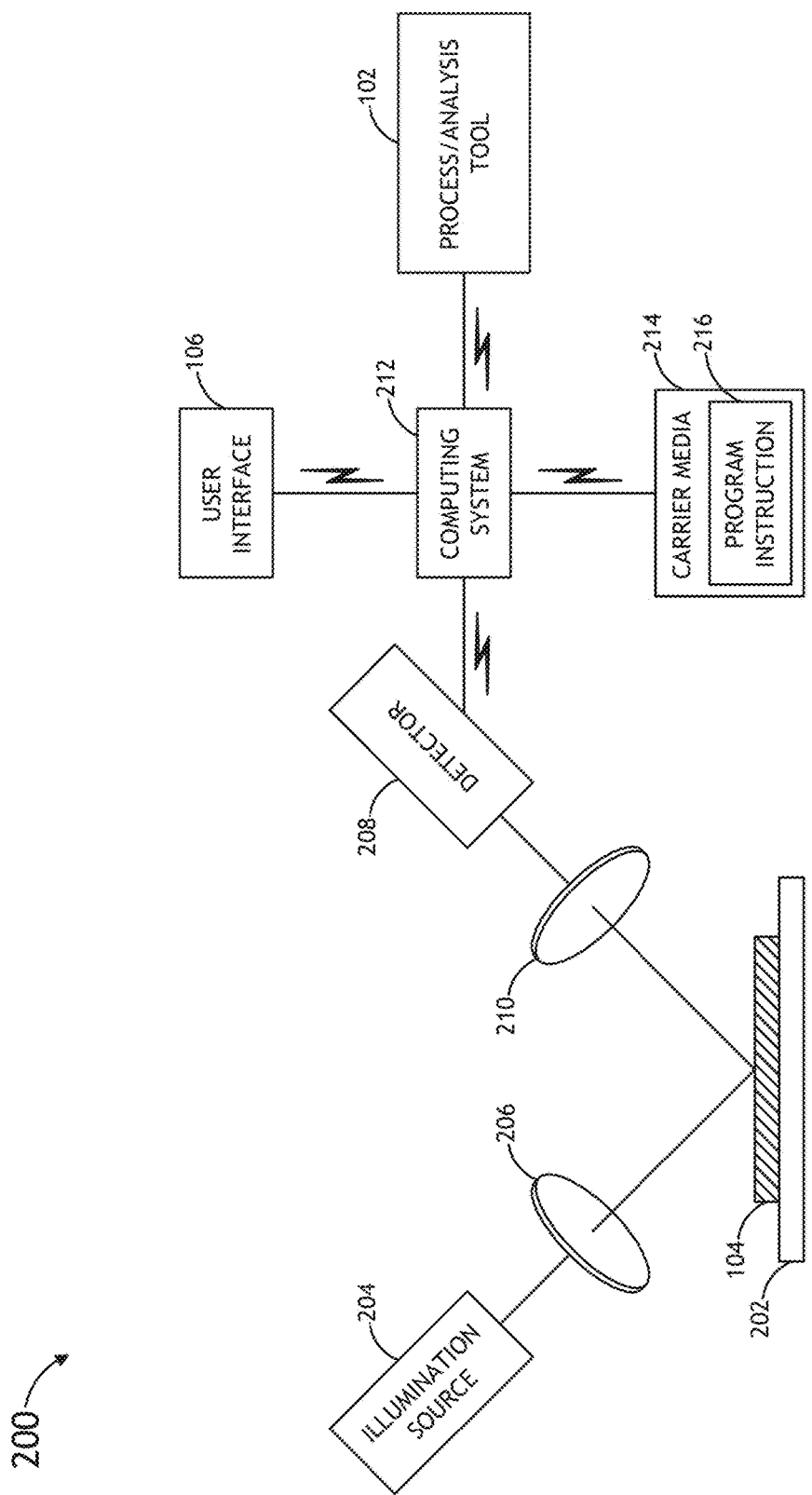
FIG. 2 is a block diagram illustrating a measurement tool of the tool matching system, in accordance with an embodiment of this disclosure.

The measurement tool 200 may include any system or device capable of determining spatial parameters or physical parameters of a wafer 104 or one or more layers of the wafer 104. For example, the measurement tool may include a metrology system, such as a reflectometer, ellipsometer, interferometer, or the like. In an embodiment, the measurement tool 200 may include an optical metrology system, as illustrated in FIG. 2. Although FIG. 2 generally illustrates an ellipsometry system, the measurement tool 200 may include any metrology system known to the art, such as spectroscopic ellipsometry systems, reflectometry systems, angle-resolved reflectometry systems, and the like. Various embodiments may include, but are not limited to, any of the metrology tools or systems discussed in U.S. Pat. Nos. 5,607,800, 5,867,276, 5,963,329, 5,739,909, 5,889,593, 6,429,943, 6,819,426, and 6,813,034, all of which are included herein by reference. Measured parameters may include, but are not limited to, film thickness, critical dimension, trench height, sidewall angle, overlay, reflectivity, or surface roughness/smoothness.

In accordance with the embodiment illustrated in FIG. 2, the measurement tool 200 may include a stage 202 configured to support the wafer 104. In some embodiments, the stage 202 may be further configured to actuate the wafer 104 to a selected location. For example, an actuator, such as a motor or gear that is mechanically coupled to the stage 202 may be configured to rotate or translate the stage 202 to position the wafer 104. Alternatively, a contactless actuator, such as a magnetic suspension mechanism, may be configured to actuate the stage 202. The wafer 104 may include a control wafer having known parameters. For example, one or more control wafers may be suspended at a particular stage of processing to maintain selected parameters within an expected set of ranges. Alternatively, the wafers 104 run through the metrology system 200 may be product wafers, wherein a feedback loop enables parameter deviations to be tracked from run to run.

The measurement tool 200 may further include at least one illumination source 204 configured to provide illumination along an illumination path to illuminate at least one portion of the wafer 104. The illumination path may include a direct line of sight between the illumination source 204 and the wafer 104. Alternatively, the illumination path may be delineated by an arrangement of one or more optical elements 206, such as retarders, quarter wave plates, focus optics, phase modulators, polarizers, mirrors, beam splitters, prisms, reflectors, converging/diverging lenses, and the like. The illumination optics 206 may be configured to filter, focus, attenuate, and/or modulate illumination transferred along the illumination path to the illumination portion of the wafer 104. For example, the illumination optics 206 may include a polarizer and a focusing lens configured, respectively, to polarize and focus illumination delivered to the illuminated portion of the wafer 104.

The measurement tool 200 may further include at least one detector 208 configured to receive illumination reflected, scattered, or radiated from the illuminated portion of the wafer 104. Illumination reflected, scattered, or radiated from the wafer 104 may be directed to the detector 208 or a set of detectors along at least one detection path. The detection path may include a direct line of sight between the detector 208 and the illuminated portion of the wafer 104. Alternatively, the detection path may be delineated by one or more optical elements 210, as was previously discussed with regards to the illumination path. Detection optics 210 disposed along the detection path may be configured to filter, focus, attenuate, and/or modulate illumination reflected, scattered, or radiated from the wafer 104. For example, the detection optics 210 may include an analyzer and a delivery lens configured, respectively, to polarize and focus illumination delivered to the detector 208.

The foregoing arrangements are included for illustrative purposes and should not be interpreted as limitations on the present disclosure. It is contemplated that the measurement tool 200 may include any number of illumination sources 204, detectors 208, optics 206/210 arranged in any metrology configuration known to the art. Further, the measurement tool 200 may include alternative probing/detection technologies (e.g. electron-beam sources/detectors). Any measurement technology now or hereafter known to the art may be utilized without departing from the scope of this disclosure.

As discussed above, the measurement tool 200 may further include at least one computing system 212 communicatively coupled to the one or more detectors 208 (i.e. optical detectors illustrated in FIG. 2 or alternative detectors, such as those including electrical, magnetic, or physical force sensors). As used herein, the term "communicatively coupled" may refer to a direct (wired) connection, a wireless connection, and/or a networked or switched connection for receiving measured data from the one or more detector 208. In some embodiments, the computing system 212 may be detached from the measurement tool 200 and alternatively configured to receive the measured data via a portable carrier medium, such as a flash drive or an external hard drive. In some embodiments, a plurality of communicatively coupled or detached computing systems may be configured to jointly perform the steps, functions, or operations performed by the "computing system 212" described herein. Those skilled in the art will appreciate that any number and/or arrangement of computing systems 212 can be utilized without departing from the scope of this disclosure.

Figure 3A:
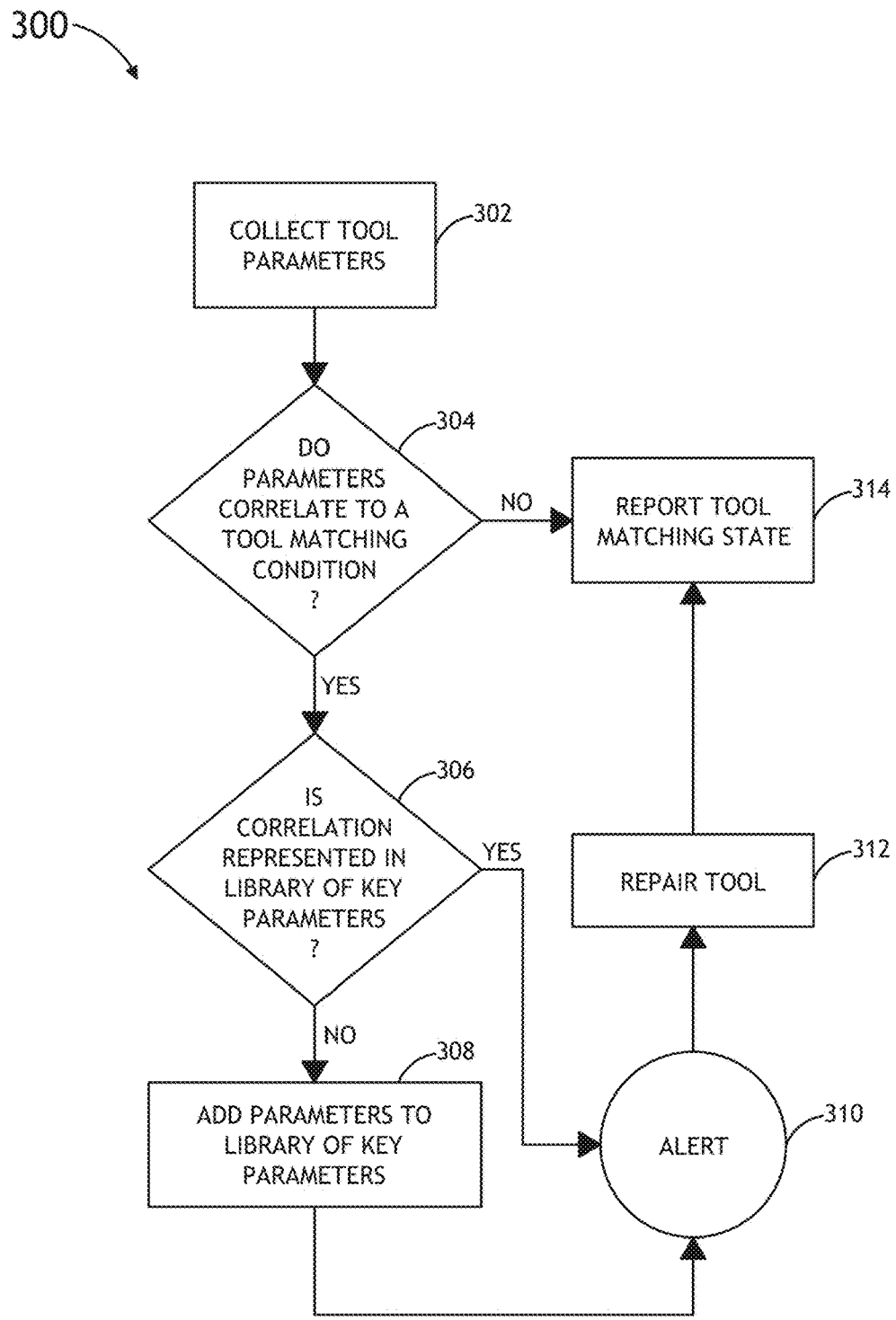
FIG. 3A is a flow diagram illustrating a method of tool matching, in accordance with an embodiment of this disclosure.
Figure 3B:
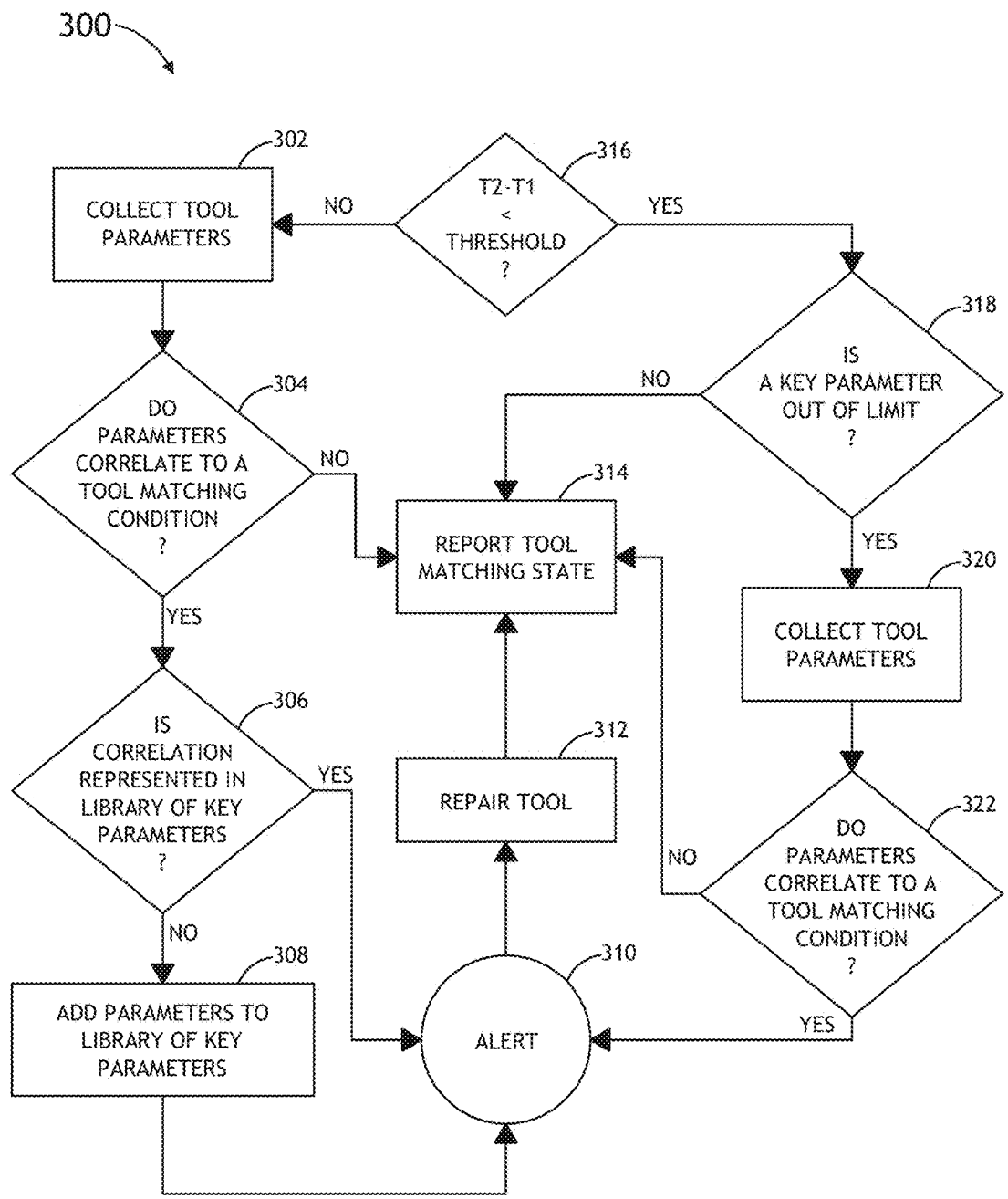
FIG. 3B is a flow diagram illustrating a method of tool matching, in accordance with an embodiment of this disclosure.

FIGS. 3A and 3B are flow diagrams illustrating a method 300 of tool matching according to various embodiments of this disclosure. The method 300 may be manifested by embodiments of system 100. For example, various steps of method 300 may carried out via the measurement tool 200 and/or implemented via one or more instruction sets embedded in the program instructions 216 which are executed by the computing system 212 that is included in or communicatively coupled with the measurement tool 200. Method 300 may further include steps for performing one or more of the functions or operations described above with regard to one or more embodiments of the system 100 and/or the measurement tool 200. However, method 300 is not limited by the foregoing embodiments of system 100 or measurement tool 200. Method 300 may be further manifested by any device or combination of devices configured to perform one or more of the following steps.

Looking now to FIG. 3A, the method 300 includes a step 302 of performing measurements upon at least one control wafer 104 to measure a set of parameters. In an embodiment shown in FIG. 2, for example, the computing system 212 may be configured to determine the set of parameters based upon detected illumination that is reflected, scattered, or radiated from the wafer 104. Alternatively, the computing system 212 may be configured to receive the measured set of parameters from an optical metrology tool or any other measurement tool 200 via a communication link/network or a portable carrier medium. One or more of the measured parameters of the control wafer 104 may be correlated with various conditions of the tool 102 being matched. For example, deviations in one or more of the parameters may be indicative of a correctable tool condition, such as a drift or misalignment of an optical element or mechanical component of the tool, debris buildup on a tool surface or junction, one or more damaged tool components, or the like.

At step 304, a comparison is made between the measured set of parameters and a primary set of parameter thresholds. The primary set of parameter thresholds may be a full or comprehensive list of parameter thresholds, which may be updated from time to time utilizing a feedback or feedforward loop. For example, the parameter thresholds may be adjusted based upon measurements collected from control or product wafers after a repair is performed upon the tool 102 (i.e. after a correlated correctable tool condition is removed and tool health is restored). At step 304, if the measured parameters are all within threshold limits and/or a threshold violation is present but no tool matching condition, the method 300 proceeds to step 314 where the tool matching state is reported to the tool 102 and/or via a user interface 106. For example, when there are no tool matching conditions, the tool matching state may include information regarding presence or absence of threshold/limit violations, absence of any needed repairs needed, and the like.

The method 300 proceeds to step 306 if one or more of the parameters are in violation of the parameter thresholds and the one or more parameter threshold violations are matched with a correctable tool condition. At step 306, a comparison is made between the matched parameters and a library of key parameters to determine whether or not the tool matching correlation between the matched parameters and the identified correctable tool condition is represented in the library. If the correlation is known, then the method 300 proceeds to step 310 where an alert is sent to the tool 102 and/or communicated to a user via the user interface 106. The alert may include information about the correctable tool condition and, in some embodiments, may further include or may be accompanied with a control signal (in the case of automatic repairs) or instructions for repairing the tool to eliminate the correctable tool condition.

If the correlation is unknown, then the method 300 also proceeds to step 308 before/after step 310. At step 308, the matched parameters are added to the library of key parameters. The library of key parameters may include a secondary set of parameter thresholds that is smaller than the primary set of parameter thresholds. For example, the secondary set of parameter thresholds may include only thresholds of the key/critical parameters. As additional runs are performed, the library is updated with new key parameters. Thus, the key parameters (i.e. those which are highly correlated with certain tool conditions) are automatically learned. As discussed in further detail below, these key parameters are monitored on a more frequent basis to detect threshold violations that may be of interest.

At step 312, repairs on the tool are performed by a user in response to the alert and/or instructions communicated via the user interface 106, or the repairs are automatically carried by the tool 102 in response to the alert and/or control signals transmitted to the tool 102. In some embodiments, for example, the tool 102 may be automatically repaired by reconfiguration of control settings (e.g. actuator, illumination source, and/or detector settings) or repositioning of (motorized) optical elements or components in response to the alert and/or control signal. In other embodiments, the alert may include one or more instructions to replace, clean, or adjust at least one optical element or mechanical component of the tool and/or instructions to reconfigure at least one control setting of an actuator, an illumination source, or a detector of the tool. The method 300 may further proceed to step 314, where the tool matching state is reported to the tool 102, a host controller or system monitor, or via the user interface 106. When repairs have been performed, the tool matching state may include, for example, information regarding the repair, the correctable tool condition, affected parameters, and the like.

As shown in FIG. 3B, the method 300 continues to monitor control wafers and/or product wafers at scheduled, manually-selected, or event-driven times. In some embodiments, the method 300 may continue to monitor product wafers from run-to-run or at scheduled times in the background. To allow for more frequent or continual monitoring, at step 316, a comparison between the current run time (hereinafter referred to as the "second time") and the subsequent run time (hereinafter referred to as the "first time"). When the difference between the second time and the first time is less than a threshold time difference (or threshold number of runs), the method 300 proceeds to step 318 where a second set of parameters are measured on a second wafer (i.e. product or control wafer) and compared against the smaller secondary set of parameter thresholds of the library of key parameters to determine whether or not any of the key parameters of the second wafer are out of limit, that is, in violation of the key parameter thresholds.

If none of the key parameters are out of limit, the method 300 proceeds to step 314 where the tool matching state is reported to the user interface 106, to the tool 102, and/or to a fabrication host controller. This loop may continue to run in the background or at specified times. When at least one key parameter is out of limit, the method 300 proceeds to step 320 where a control wafer (i.e. the same control wafer or a second control wafer) is run to determine whether or not any tool matching conditions exist. At step 320, another set of parameters (hereinafter referred to as the "third set of parameters") is collected based upon measurements performed on the control wafer. At step 322, the third set of parameters are compared against the primary or second set of parameter thresholds to determine whether or not there is a correlation to a tool matching condition. If there is no match to a correctable tool condition, the method proceeds to step 314. If there is match to a correctable tool condition, the method proceeds to steps 310, 312, and 314.

The method may return to step 302, where a control wafer (i.e. the same control wafer or another control wafer) is run either due to scheduling, user-selection, or when sufficient time has elapsed from the first run (T1) and the second run (T2). For example, if the difference between T2 and T1 is greater than the threshold time difference at step 316, the method returns to step 302 where a third set of parameters is obtained utilizing the control wafer, and then the method proceeds through steps 304, 306, 308, 310, 312, and/or 314 depending on whether or not a tool matching condition exists. The library of key parameters is updated accordingly, and as time goes on, more key parameters are learned to enable more efficient tool matching and improved accuracy. Since the auto-learning tool matching methodology may primarily run in the background (e.g. run-to-run monitoring of key parameters) and/or may be scheduled on an as-needed basis by the user, the method 300 enables more frequent tool matching to ensure that fabrication specifications are being met and is less disruptive to the fabrication process.

In further embodiments, the tool matching parameters collected at steps 302 and 320 may not require measurements performed upon a control wafer. Tool parameters may be automatically determined or generated via sensors, such as position detectors, vibration/pressure detectors, photodetectors, electrical current/potential detectors, and/or any other internal measurement systems of the matched tool 200. The control wafer may only be necessary for an initial determination of tool matching parameters (e.g. the first set of parameters). For subsequent parameter collection, the method 300 may rely less and less on the use of control wafers and more on automatic (i.e. "waferless") detection of tool parameters to determine when tool matching conditions exist, particularly when there is known correlation between the detected parameters and a correctable tool condition already represented in the library of key parameters.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. In some embodiments, various steps, functions, and/or operations are carried out by one or more of the following: electronic circuits, logic gates, multiplexers, programmable logic devices, ASICs, analog or digital controls/switches, microcontrollers, or computing systems. A computing system may include, but is not limited to, a personal computing system, mainframe computing system, workstation, image computer, parallel processor, or any other device known in the art. In general, the term "computing system" is broadly defined to encompass any device having one or more processors, which execute instructions from a carrier medium. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A method of tool matching, comprising:
performing measurements, with one or more detectors of an optical measurement tool, on a control wafer at a first time to determine a first set of parameters associated with tool conditions of a lithography tool for processing one or more wafers different from the control wafer, wherein one or more of the first set of parameters includes at least one of film thickness, critical dimension, trench height, sidewall angle, overlay, surface roughness, or surface smoothness of the control wafer;
comparing, with one or more processors communicatively coupled to the one or more detectors of the optical measurement tool, the first set of parameters against a primary set of parameter thresholds to determine when a parameter of the first set of parameters matches a correctable tool condition;
determining, with the one or more processors, a presence or an absence of the parameter in a library of key parameters when the parameter matches the correctable tool condition, the library of key parameters including a secondary set of parameter thresholds that is a subset of the primary set of parameter thresholds;
adding, with the one or more processors, the parameter to the library of key parameters when the parameter matches the correctable tool condition and is not represented in the library of key parameters;
providing to the lithography tool, with the one or more processors, a control signal configured to reconfigure at least one control setting of the lithography tool to repair the correctable tool condition;
performing measurements on a second wafer at a second time to determine a second set of parameters;
identifying at least one of a time difference or a run count between the first time and the second time; and
comparing, when the time difference is below a threshold time difference or when the run count is below a threshold run count, the second set of parameters against the secondary set of parameter thresholds of the library of key parameters to determine when a key parameter of the second set of parameters is out of limit.

2. The method of claim 1, further comprising:
when the key parameter of the second set of parameters is determined to be out of limit, performing measurements on the control wafer to determine a third set of parameters; and
comparing the third set of parameters against the primary set of parameter thresholds to determine when a parameter of the third set of parameters matches the correctable tool condition.

3. The method of claim 1, further comprising:
when the time difference between the first time and the second time is above the threshold time difference, performing measurements on the control wafer to determine a third set of parameters; and
comparing the third set of parameters against the primary set of parameter thresholds to determine when a parameter of the third set of parameters matches the correctable tool condition.

4. The method of claim 1, further comprising:
providing an alert via a user interface when the lithography tool is determined to be affected by the correctable tool condition.

5. The method of claim 4, wherein the alert includes one or more instructions for repairing the correctable tool condition.

6. The method of claim 5, wherein the one or more instructions include instructions to replace, clean, or adjust at least one optical element or mechanical component of the lithography tool.

7. The method of claim 5, wherein the one or more instructions include instructions to reconfigure at least one control setting of an actuator, an illumination source, or a detector.

8. A system comprising:
an optical measurement tool comprising:
a stage configured to receive a control wafer;
at least one illumination source configured to illuminate the control wafer;
at least one detector configured to receive illumination reflected, scattered, or radiated from the control wafer; and
a computing system in communication with the at least one detector, the computing system including one or more processors configured to execute program instructions configured to cause the one or more processors to:
determine, based upon illumination detected from the control wafer at a first time, a first set of parameters associated with tool conditions of a lithography tool for processing one or more wafers different from the control wafer, wherein one or more of the first set of parameters includes at least one of film thickness, critical dimension, trench height, sidewall angle, overlay, surface roughness, or surface smoothness of the control wafer;
compare the first set of parameters against a primary set of parameter thresholds to determine when a parameter of the first set of parameters matches a correctable tool condition;
determine a presence or an absence of the parameter in a library of key parameters when the parameter matches the correctable tool condition, the library of key parameters including a secondary set of parameter thresholds that is a subset of the primary set of parameter thresholds;
add the parameter to the library of key parameters when the parameter matches the correctable tool condition and is not represented in the library of key parameters;
provide, to the lithography tool, a control signal configured to reconfigure at least one control setting of the lithography tool to repair the correctable tool condition;
determine a second set of parameters based upon illumination detected from a second wafer at a second time;
identify a time difference between the first time and the second time; and
compare, when the time difference is below a threshold time difference, the second set of parameters against the secondary set of parameter thresholds of the library of key parameters to determine when a key parameter of the second set of parameters is out of limit.

9. The system of claim 8, wherein the computing system is further configured to:

when the key parameter of the second set of parameters is determined to be out of limit, determine a third set of parameters based upon illumination detected from the control wafer; and compare the third set of parameters against the primary set of parameter thresholds to determine when a parameter of the third set of parameters matches the correctable tool condition.

10. The system of claim 8, wherein the computing system is further configured to:

when the time difference between the first time and the second time is above the threshold time difference, determine a third set of parameters based upon illumination detected from the control wafer; and compare the third set of parameters against the primary set of parameter thresholds to determine when a parameter of the third set of parameters matches the correctable tool condition.

11. The system of claim 8, wherein the computing system is further configured to:

provide an alert via a user interface when the lithography tool is determined to be affected by the correctable tool condition.

12. The system of claim 11, wherein the alert includes one or more instructions for repairing the correctable tool condition.

13. The system of claim 12, wherein the one or more instructions include instructions to replace, clean, or adjust at least one optical element or mechanical component of the lithography tool.

14. The system of claim 12, wherein the one or more instructions include instructions to reconfigure at least one control setting of an actuator, an illumination source, or a detector of the lithography tool.

15. A non-transitory computer readable medium having computer-executable components, wherein the computer-executable components are configured to:

determine, based upon measurements collected from a control wafer at a first time with an optical measurement tool, a first set of parameters associated with tool conditions of a lithography tool for processing one or more wafers different from the control wafer, wherein one or more of the first set of parameters includes at least one of film thickness, critical dimension, trench height, sidewall angle, overlay, surface roughness, or surface smoothness of the control wafer;

compare the first set of parameters against a primary set of parameter thresholds to determine when a parameter of the first set of parameters matches a correctable tool condition;

determine a presence or an absence of the parameter in a library of key parameters when the parameter matches the correctable tool condition, the library of key parameters including a secondary set of parameter thresholds that is a subset of the primary set of parameter thresholds;

add the parameter to the library of key parameters when the parameter matches the correctable tool condition and is not represented in the library of key parameters;

provide, to the lithography tool, a control signal configured to reconfigure at least one control setting of the lithography tool to repair the correctable tool condition;

determine a second set of parameters based upon measurements collected from a second wafer at a second time;

identify a time difference between the first time and the second time; and compare, when the time difference is below a threshold time difference, the second set of parameters against the secondary set of parameter thresholds of the library of key parameters to determine when a key parameter of the second set of parameters is out of limit.

16. The non-transitory computer readable medium of claim 15, wherein the computer-executable components are configured to:

when the key parameter of the second set of parameters is determined to be out of limit, determine a third set of parameters based upon measurements collected from the control wafer; and compare the third set of parameters against the primary set of parameter thresholds to determine when a parameter of the third set of parameters matches the correctable tool condition.

17. The non-transitory computer readable medium of claim 15, wherein the computer-executable components are configured to:

when the time difference between the first time and the second time is above the threshold time difference, determine a third set of parameters based upon measurements collected from the control wafer; and compare the third set of parameters against the primary set of parameter thresholds to determine when a parameter of the third set of parameters matches the correctable tool condition.

* * * * *